United States Patent
Heiner et al.

(10) Patent No.: US 6,547,785 B1
(45) Date of Patent: Apr. 15, 2003

(54) CRYOABLATION CATHETER FOR LONG LESION ABLATIONS

(75) Inventors: Wilfred Peter Heiner, Bakkeveen (NL); Bart-Jan Korteling, Mission Viejo, CA (US)

(73) Assignee: Biosense Webster, Inc., Diamond Bar, CA (US)

(*) Notice: Subject to any disclaimer, the term of this patent is extended or adjusted under 35 U.S.C. 154(b) by 0 days.

(21) Appl. No.: 10/001,360

(22) Filed: Oct. 23, 2001

(51) Int. Cl.[7] ................................................ A61M 5/20
(52) U.S. Cl. ........................................ 606/21; 604/113
(58) Field of Search .................. 606/20–26; 604/113, 604/6.13; 607/96, 104, 105

(56) References Cited

U.S. PATENT DOCUMENTS

| | | | |
|---|---|---|---|
| 4,985,015 A | * 1/1991 | Obermann et al. | 604/67 |
| 5,041,092 A | * 8/1991 | Barwick | 604/104 |
| 5,281,213 A | 1/1994 | Milder et al. | |
| 5,281,215 A | 1/1994 | Milder | |
| 5,423,807 A | 6/1995 | Milder | |
| 5,623,943 A | * 4/1997 | Hackett et al. | 600/585 |
| 5,630,427 A | * 5/1997 | Hastings | 604/524 |
| 5,855,546 A | 1/1999 | Hastings et al. | |
| 5,899,899 A | 5/1999 | Arless et al. | |
| 5,971,983 A | 10/1999 | Lesh | |
| 6,385,472 B1 | * 5/2002 | Hall et al. | 600/374 |
| 6,413,222 B1 | * 7/2002 | Pantages et al. | 600/466 |
| 6,454,717 B1 | * 9/2002 | Pantages et al. | 600/466 |

* cited by examiner

*Primary Examiner*—Michael Peffley
*Assistant Examiner*—Peter J Vrettakos
(74) *Attorney, Agent, or Firm*—Henry W. Collins

(57) ABSTRACT

The present invention relates to a cryoablation catheter, comprising an outer tubular body with a closed distal end to form a fluid cooling chamber and an inner tubular member having a proximal end adapted to receive fluid suitable for cryoablation and a distal end coupled to a fluid expansion nozzle wherein the inner tubular member is movable in an axial direction to thereby change the position of the nozzle within the fluid cooling chamber.

9 Claims, 3 Drawing Sheets

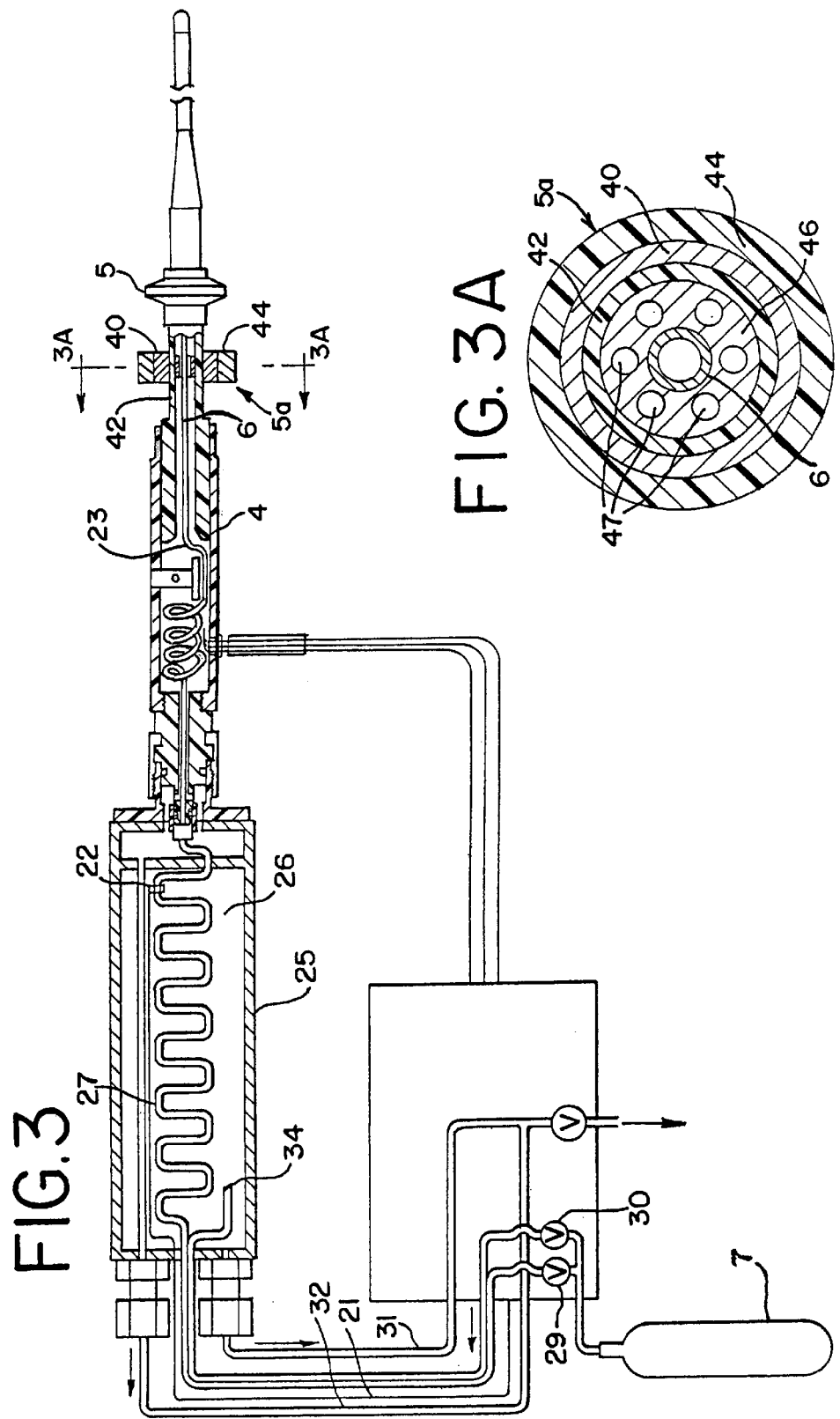

CRYOABLATION CATHETER FOR LONG LESION ABLATIONS

BACKGROUND OF THE INVENTION

1. Field of the Invention

The present invention relates to a cryoablation catheter, and more particularly to a cryoablation catheter for creating long lesions.

2. Description of the Prior Art

Many medical procedures are performed using minimally invasive surgical techniques wherein one or more slender implements are inserted through one or more small incisions into a patient's body. With respect to ablation, the surgical implement may include a rigid or flexible structure having an ablation device at or near its distal end that is placed adjacent to the tissue to be ablated. Radio frequency energy, microwave energy, laser energy, extreme heat, and extreme cold may be provided by the ablation device to destroy the tissue.

With respect to cardiac procedures, cardiac arrhythmia may be treated through selective ablation of cardiac tissue to eliminate the source of the arrhythmia. A popular minimally invasive procedure, radio frequency (RF) catheter ablation, includes a preliminary step of conventional mapping followed by the creation of one or more ablated regions (lesions) in the cardiac tissue using RF energy. Multiple lesions are frequently required. Often, five lesions, and sometimes as many as twenty lesions may be required before a successful result is attained. Sometimes only one of the lesions is actually effective.

Deficiencies of radio frequency ablation devices and techniques have been to some extent overcome by cryogenic mapping and ablation. Such cryogenic mapping techniques are in U.S. Pat. Nos. 5,423,807; 5,281,213 and 5,281,215. However, even though combined cryogenic mapping and ablation devices often times permit greater certainty and less tissue damage than RF devices and techniques, both cryogenic and RF ablation devices are usually configured for spot or circular tissue ablation.

Spot tissue ablation is acceptable for certain procedures. However, other procedures may be more therapeutically effective if multiple spot lesions are made along a predetermined line, or a single elongate or linear lesion is created in a single ablative step. Radio frequency ablation devices are known to be able to create linear lesions by dragging the ablation tip along a line while the ablation electrode is energized. U.S. patent application Ser. No. 09/518,044 entitled, "Cryoablation Catheter For Long Lesion Ablations," assigned to the same assignee as the present invention disclosing the concept of "dragging" the ablation tip, or the cooling tip, of a cryoablation catheter along a line in order to create a long lesion. In order to accomplish this function, the cryogenic cooling nozzle is moved longitudinally along the inside of a cooling chamber to thereby cause the outer surface of the cooling chamber to be cooled along a linear path which in turn creates a linear lesion along the path.

SUMMARY OF THE INVENTION

In accordance with one aspect of the present invention there is provided a cryoablation catheter system for creating linear lesions which includes an outer tubular member capable of insertion into the vessels of the body, a ceiling cap disposed at the distal end of the outer tubular member for forming a cooling chamber at the distal end of the tubular member, an inner tubular member slidably disposed within the outer tubular member. The proximal end of the inner tubular member is adapted to receive a fluid, such as nitrous oxide. A fluid expansion nozzle, such as a Joule-Thompson nozzle, is disposed on the distal end of the inner tubular member. The catheter system also includes a nozzle control system which is comprised of an inner ring member formed of a magnetic material which is mounted on the proximal end of the inner tubular member, and an outer ring member formed of magnetic material which is slidably mounted on the outer tubular member. Because of the magnetic attraction between these two magnetic members, when the outer ring member is moved along the outer tubular member it "pulls" or draws the inner magnetic ring member along with the outer magnetic ring member to thereby cause the inner tubular member to be moved longitudinally which in turn causes the fluid expansion nozzle to be moved longitudinally within the cooling chamber.

In accordance with another aspect of the present invention, the inner tubular member is disposed coaxially within the outer tubular member so as to define a passageway between the inner tubular member and the outer tubular member, and a cylindrical support member is disposed between the inner tubular member and the outer tubular member for supporting the inner tubular member for movement within the cooling chamber. The cylindrical support member includes at least one passageway which extends through the support member to permit fluid, such as, nitrous oxide, to be returned through the passageway for removal from the catheter system. In accordance with still another aspect of the present invention, the inner magnetic ring member is disposed coaxially within the outer tubular member and extends in the passageway between the inner tubular member and the outer tubular member, and includes at least one passageway which extends through the inner magnetic ring member to permit fluid to be returned through the passageway for removal from the catheter. In accordance with still another aspect of the present invention, the fluid expansion nozzle takes the form of a Joule-Thompson nozzle which is disposed on the distal end of the inner tubular member.

With the nozzle control system of the present invention, it is possible to provide a cryoablation catheter system for creating linear lesions by moving the fluid expansion nozzle in a longitudinal direction along the interior of the cooling chamber while maintaining an entirely sealed catheter system. In other words, by use of magnetic attraction which exists from an external ring magnet and an internal ring magnet it is possible to "pull" the fluid expansion nozzle along a longitudinal path within the sealed cooling chamber while maintaining a hermetically sealed catheter system.

These and other objects of the present invention will become more apparent when considered in view of the following description of a preferred embodiment of the present invention.

BRIEF DESCRIPTION OF THE DRAWINGS

Further properties, advantages and measures according to the present invention will be explained in greater detail in the description of a preferred embodiment, with reference to the attached figures in which:

FIG. 3 illustrates in detail the proximal end of the cryoablation catheter, the control handle and the coolant system including the cooling nozzle control system in more detail; and FIG. 3A illustrates in more detail a cross sectional view of the cooling nozzle control system.

DESCRIPTION OF THE PREFERRED EMBODIMENT

Figure 1:
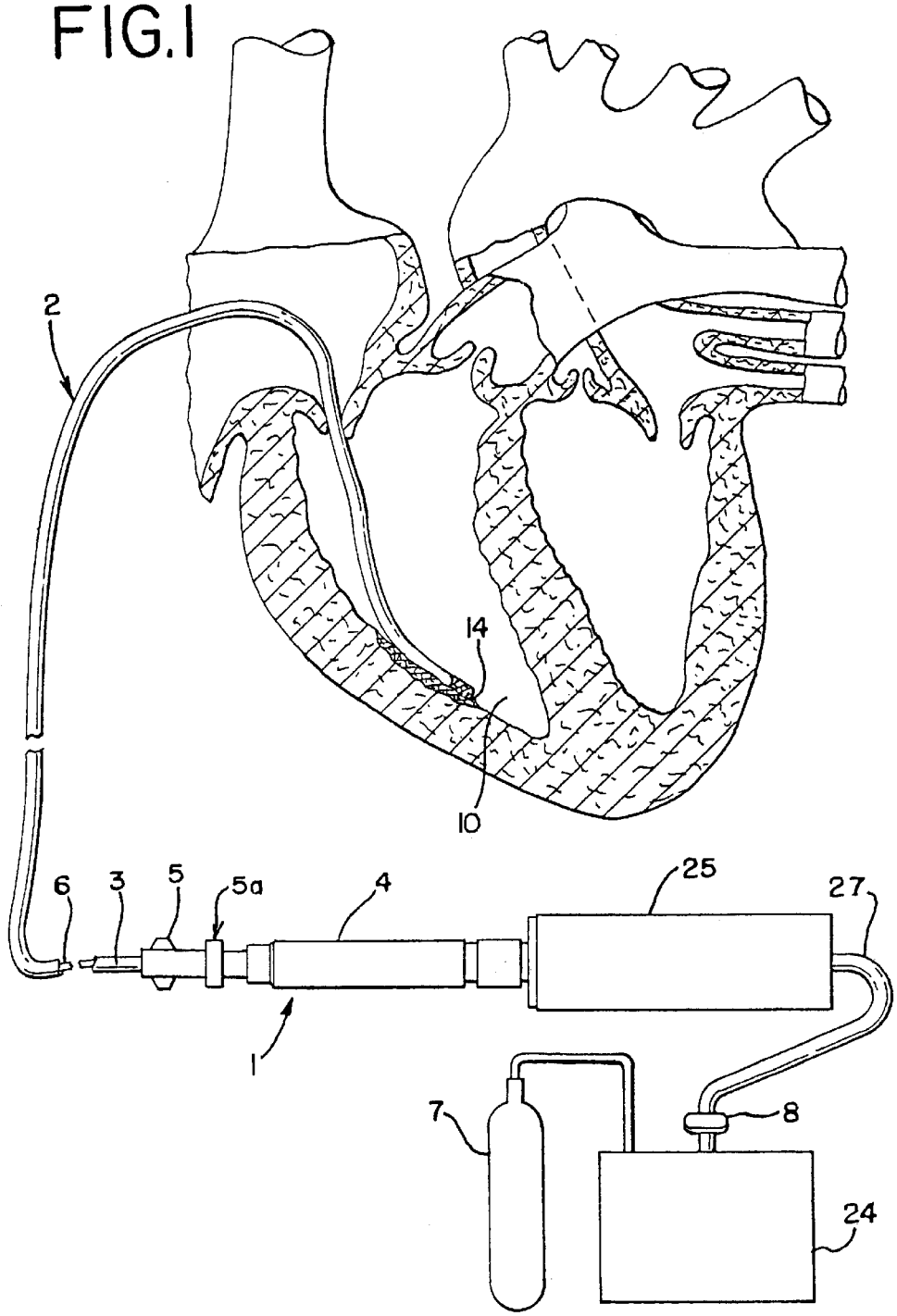
FIG. 1 is a schematic view of a system for cryoablation with a catheter according to the present invention placed within a human heart.

In FIG. 1 a cryoablation catheter system 1 according to the present invention has been illustrated with a catheter 2. The catheter 2 comprises an outer body 3, an inner body 6, a handle 4 and a deflection knob 5. The deflection knob 5 is connected with the inner body 6 and the handle 4 with the outer body 3, whereby the deflection knob 5 is movable in the axial direction of the catheter 2 in relation to the handle 4 in such a way that the distal tip of the inner body 6, where the inner body 6 opens out into the lumen of the outer body 3, is movable in an axial direction with respect to the distal tip of the catheter 2.

The deflection knob 5 is connected via a heat exchanger 25, a connecting tube 27 through a control unit 24 and a valve 8 with a gas cylinder 7, containing $N_2O$. By way of an alternative, or as an addition, also other substances than $N_2O$ may be used. Preferably, a fluid is used of which the cooling effect only occurs on expansion when it is ejected via the inner body 6 close to the distal end of the catheter 2 into the lumen of the outer body 3. This fluid will expand, as a result of which the a cooling effect will be achieved. $N_2O$ meets this requirement with satisfactory results.

As illustrated in FIG. 1 the valve 8 constitutes the control means with which the flow of $N_2O$ through the inner body 6, and the pressure inside this inner body 6 is regulated. The pressure depends on the intended effect of the cryoablation at the distal tip of the catheter 2. In an embodiment of the present invention not illustrated here, the catheter 2 has been provided near to the distal end with measuring equipment, such as a thermocouple, which also forms part of the control means, in which case the valve 8 is activated on the basis of the measuring results obtained at the thermocouple. In that case the measurement of the temperature is set to a target value established in advance, in order to effect the required degree of cryoablation.

The tip at the distal end of the catheter 2 may also be provided with other measurement equipment to determine the position of the nozzle 12 for instance. Examples of such measuring equipment are marking rings which are recognizable when using imaging techniques like MRI or when using x-ray radiation. Equipment to determine whether the surrounding tissue also needs to be ablated may be included here as well.

In the situation illustrated in FIG. 1, the distal end of the catheter 2 has been introduced into a chamber of the heart 10 and advanced to a position where tissue 14 is located which is suitable for ablation. It could however also concern here applications in a vein or at any other location. The only thing which is important, is that in the body cavity there is tissue, like the tissue 14 illustrated here, which qualifies for ablation.

Figure 2:
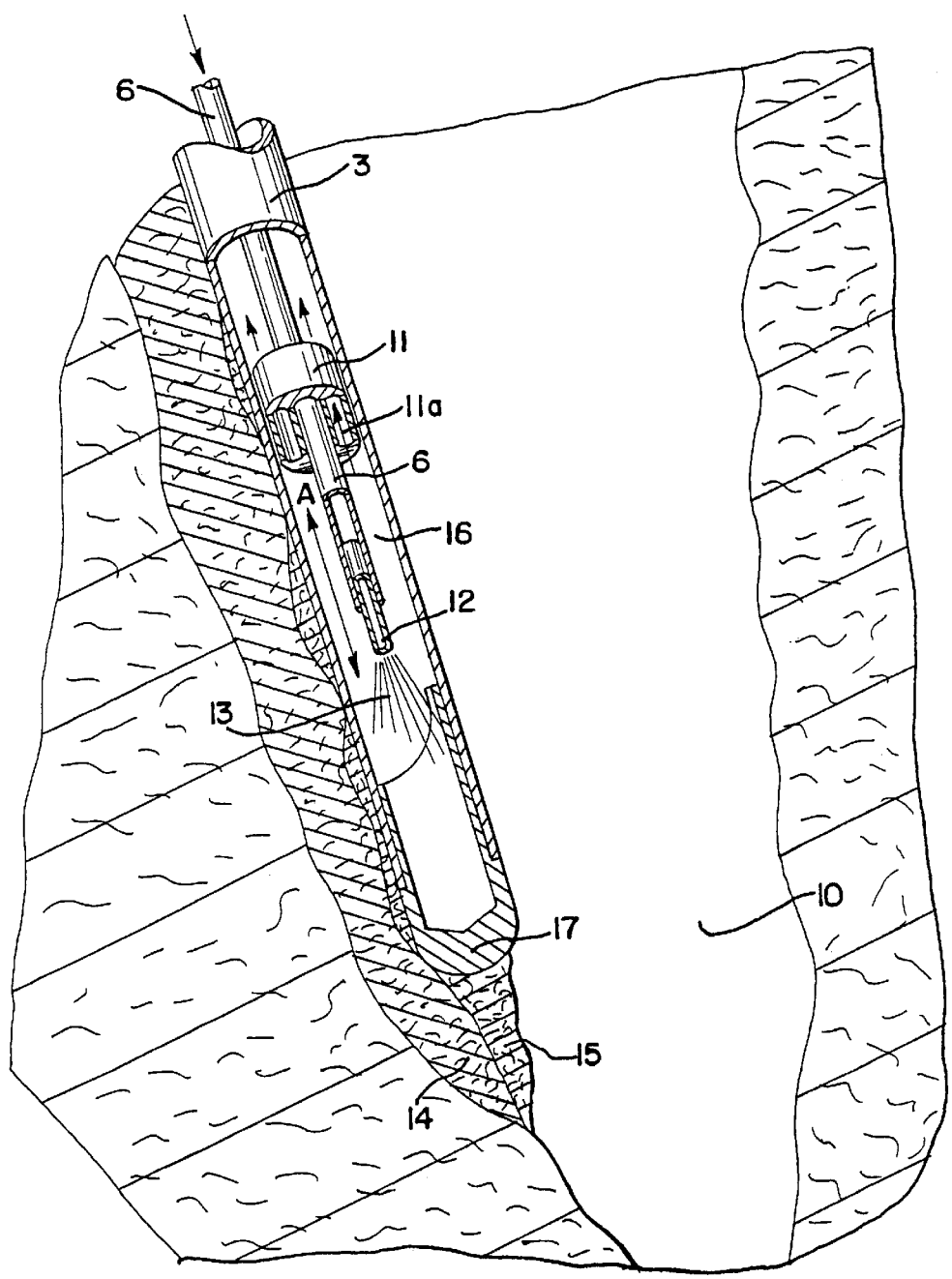
FIG. 2 illustrates in detail the distal tip of the cryoablation catheter according to the present invention placed within a human heart.

FIG. 2 is a detailed and partly cross-sectional view of the distal end of the catheter 2 in a position for use. The inner body 6 opens out into the internal lumen 16 of the outer body 3 close to the distal end of the catheter. Through the inner body 6 a flow of $N_2O$ coolant is supplied, which is ejected via a nozzle 12, which preferably takes the form of a Joule-Thompson nozzle, so that a cold zone 13 is created. In the immediate proximity of this cold zone 13, at the nozzle 12 of the inner body 6, the coldness created on the outside of the outer body 3 is such that ice 15 is formed and the tissue 14 is ablated.

As has been described in connection with FIG. 1, the deflection knob 5, which is connected with the inner body 6, is movable in relation to the handle 4, which is connected with the outer body 3. In this manner the nozzle 12 at the distal end of the inner body 6 is moved in relation to the outer body 3. In the situation illustrated here, the outer body 3 on the other hand has in the meantime become stuck in the ice 15, and is consequently no longer movable. The inner body 6 and, in particular in the proximity of the nozzle 12 hereof, a sliding block 11 has been arranged around the inner body 6 close to the nozzle 12, which functions as a distancing body. The dimensions of the sliding block 11 correspond to those of the internal lumen 16 of the outer body 3, so that it can move freely up and down in the outer body 3 in the direction indicated by arrow "A," in which changes can be made in the position of the nozzle 12. The sliding block 11 also includes passageways 11a which extend through the sliding block. The sliding block 11 is provided with the passageways 11a to allow the coolant fluid to flow back from the cooling chamber.

All components of the catheter illustrated here have preferably been made of materials which do not shrink together due to expansion or contraction of the materials.

In the embodiment illustrated here, the outer body 3 has been closed off by means of a closure 17.

The catheter system illustrated in FIG. 3 includes a catheter 2. The proximal end of the catheter 2 carries a handle 4, with which the catheter has been received in the deflection knob 5. A pressure line 23 extends from the proximal end of the catheter 2 to the distal end. The pressure line 23 supplies high pressure refrigerant to the distal end of the catheter.

FIGS. 3 and 3A also illustrate in more detail the nozzle positioning mechanism 5a which is comprised of an outer ring 40 formed of a magnetic material which is slidably mounted on a cylindrical piston 42. The outer magnetic ring is hermetically sealed within a polymer layer 44. An inner ring 46 extends around and is fixedly attached to the inner body 6. The inner ring 46 is also formed of a magnetic material. In addition, the inner magnetic ring includes multiple passageways 47 which serve to permit the cooled fluid to be removed from the catheter system 2. As previously described, the cooling nozzle 12 is mounted on the distal end of the inner body 6. Accordingly, as the outer magnetic ring 40 is moved along the cylindrical piston 42, it causes the inner magnetic ring 46 to be pulled along through magnetic attraction. As the inner ring 46 is pulled along, it causes the inner body to be moved which in turn draws the cooling nozzle 12 along a longitudinal path through the cooling chamber. Accordingly, the wall of the cooling chamber is cooled along the path of travel of the cooling nozzle 12. This path of travel creates a linear lesion along the line of contact between the cooling chamber and adjacent tissue.

The expanded gaseous fluid flows, via the discharge channel formed by the internal lumen 16 in the catheter body and through the passageways 11a back to the proximal end of the catheter. The discharge channel of the catheter body is connected in a suitably sealed-off manner with the line 32 in the deflection knob 5.

To achieve sufficient cooling effect in the tip of the catheter 2, the refrigerant is pre-cooled in the heat exchanger 25, before it is introduced into the catheter. The cooling means illustrated schematically in FIG. 3 comprises an insulated cooling chamber 26, through which a connecting pressure tube 27 extends in a helical pattern. The pressure line 23 is connected with this connection tube 27. The fluid under pressure is supplied to the connection tube 27 from a refrigerant source illustrated here as a gas cylinder 7. The required quantity is regulated by means of the adjustable valve 29.

Preceding the valve 29 a line branches off from the refrigerant line which, via a restriction 34, opens out into the cooling chamber 26. The quantity of fluid supplied to the cooling chamber 26 is regulated by the size and the dimensions of the restriction 34 and the control valve 30. On passing the restriction 34 the refrigerant expands in the chamber 26 and removes heat from the surroundings, that is to say from the refrigerant flowing through the connecting tube 27 which is cooled as a result. The expanded fluid is extracted from the chamber 26 through the line 31, so that a sufficient pressure difference is maintained across the restriction.

As shown in FIG. 3, a temperature sensor 22 has been arranged at the proximal end of the pressure line, which is connected via a signal line 21 with a temperature measuring device. In this way it is possible to check the temperature of the refrigerant supplied to the proximal end of the pressure line 23. The control valve 30 may be regulated on the basis of the temperature measured. In another embodiment, the control valve 30 may be regulated by a control means on the basis of the temperature measured with the sensor 22.

A temperature sensor (not shown) may also be placed at the tip of the catheter 2. By means of this temperature sensor the temperature at the tip of the catheter 2 may be monitored. The value measured by this sensor may be used to adjust the adjustable valve 29. Alternatively, the adjustable valve 29 may be regulated automatically in response to the temperature measured at the tip.

The catheter device according to the invention is for instance used to ablate surface tissue inside the heart, when treating certain cardiac arrhythmias.

Because of the relatively high heat resistance coefficient of the material of which the pressure line 23 has been made, the pre-cooled fluid will at the most absorb only little heat from the surroundings. Inside the outer body 3 of the catheter 2 the pressure line 23 forming the inner body 6 extends through the central lumen. The expanded gas which is being removed from the tip flows through this lumen. This expanded gas has initially a very low temperature and is only heated to limited degree in the tip. The gas flowing through the lumen 16 forming the discharge channel consequently still has a low temperature, so that as a result none or only little heating of the refrigerant supplied under pressure will take place.

It should be noted that only a possible embodiment has been illustrated. Other embodiments are possible as well. The heat exchanger 25 for instance may be integrated into the deflection knob 5. The pressure line 23 may in that case be surrounded along more or less its entire length by expanded fluid which is being discharged, so that the temperature of the pressure fluid may be controlled accurately. Alternatively, the nozzle configuration may be radially placed inside the distal end of the pressure tube, or in other possible configurations.

These modifications would be apparent to those having ordinary skill in the art to which this invention relates and are intended to be within the scope of the claims which follow.

That which is claimed is:

1. A cryoablation catheter system for creating linear lesions comprising:

an outer tubular member having a proximal end and a distal end and being capable of insertion into the vessels of the body;

a sealing cap disposed at the distal end of the outer tubular member for forming a cooling chamber at the distal end of the outer tubular member;

an inner tubular member slidably disposed within the outer tubular member and having a proximal end and a distal end, the proximal end of the inner tubular member being adapted to receive a fluid which cools when expanded;

a fluid expansion nozzle disposed on the distal end of the inner tubular member; and, a nozzle control system comprising an inner ring member formed of a magnetic material fixedly mounted on the proximal end of the inner tubular member, and an outer ring member formed of a magnetic material slidably mounted on the outer tubular member which when moved along the outer tubular member causes the inner magnetic ring member to be pulled along with the outer magnetic ring member to thereby cause the inner tubular member to be moved longitudinally thereby causing the fluid expansion nozzle to be moved longitudinally within the cooling chamber.

2. A cryoablation catheter system as defined in claim 1, wherein the inner tubular member is disposed coaxially within the outer tubular member so as to define a passageway between the inner tubular member and the outer tubular member; and, a cylindrical support member is disposed between the inner tubular member and the outer tubular member, said support member having at least one passageway which extends through the support member to permit fluid to be returned through the passageway for removal from the catheter system.

3. A cryoablation catheter system as defined in claim 2, wherein the inner magnetic ring member is disposed coaxially within the outer tubular member and extends in the passageway between the inner tubular member and the outer tubular member; and, Said inner magnetic ring member has at least one passageway which extends through the inner magnetic ring member to permit fluid to be returned through the passageway for removal from the catheter system.

4. A cryoablation catheter system comprising a cryoablation catheter including:

an outer tubular member having a proximal end and a distal end and being capable of insertion into the vessels of the body;

a sealing cap disposed at the distal end of the outer tubular member for forming a cooling chamber at the distal end of the catheter;

an inner tubular member slidably disposed within the outer tubular member and having a proximal end and a distal end;

a Joule-Thompson nozzle disposed on the distal end of the inner tubular member;

a nozzle control system comprising an inner ring member formed of a magnetic material fixedly mounted on the proximal end of the inner tubular member, and an outer ring member formed of a magnetic material slidably mounted on the outer tubular member which when moved along the outer tubular member causes the inner magnetic ring member to be pulled along with the outer magnetic ring member to thereby cause the inner tubular member to be moved longitudinally thereby causing the Joule-Thompson nozzle to be moved longitudinally within the cooling chamber;

a source of a high pressure gas coupled to the proximal end of the inner tubular member; and, a control valve for varying the pressure of a high pressure gas for varying the flow of gas to the Joule-Thompson nozzle.

5. A cryoablation catheter system as defined in claim 4, wherein the inner tubular member is disposed coaxially within the outer tubular member so as to define a passageway between the inner tubular member and the outer tubular member; and, a cylindrical support member is disposed between the inner tubular member and the outer tubular member, said support member having at least one passageway which extends through the support member to permit fluid to be returned through the passageway for removal from the catheter.

6. A cryoablation catheter system as defined in claim 5, wherein the inner magnetic ring member is disposed coaxially within the outer tubular member and extends in the passageway between the inner tubular member and the outer tubular member; and, said inner magnetic ring member has at least one passageway which extends through the inner ring magnetic member to permit fluid to be returned through the passageway for removal from the catheter.

7. A cryoablation catheter system comprising:

an outer tubular member having a proximal end and a distal end and being capable of insertion into the vessels of the body;

a sealing cap disposed at the distal end of the outer tubular member for forming a cooling chamber at the distal end of the outer tubular member;

an inner tubular member slidably disposed within the outer tubular member and having a proximal end and a distal end, the proximal end of the inner tubular member being adapted to receive a fluid which when expanded cools to an extremely low temperature;

a Joule-Thompson nozzle disposed on the distal end of the inner tubular member; and, a nozzle control system comprising an inner ring member formed of a magnetic material fixedly mounted on the proximal end of the inner tubular member, and an outer ring member formed of a magnetic material slidably mounted on the outer tubular member which when moved along the outer tubular member causes the inner magnetic ring member to be pulled along with the outer magnetic ring member to thereby cause the inner tubular member to be moved longitudinally thereby causing the Joule-Thompson nozzle to be moved longitudinally within the cooling chamber.

8. A cryoablation catheter system as defined in claim 7, wherein the inner tubular member is disposed coaxially within the outer tubular member so as to define a passageway between the inner tubular member and the outer tubular member; and, a cylindrical support member is disposed between the inner tubular member and the outer tubular member, said support member having at least one passageway which extends through the support member to permit fluid to be returned through the passageway for removal from the catheter system.

9. A cryoablation catheter system as defined in claim 8, wherein the inner magnetic ring member is disposed coaxially within the outer tubular member and extends in the passageway between the inner tubular member and the outer tubular member; and, said inner magnetic ring member has at least one passageway which extends through the inner ring member to permit fluid to be returned through the passageway for removal from the catheter system.

* * * * *